United States Patent [19]
Sekiguchi et al.

[11] Patent Number: 5,997,496
[45] Date of Patent: Dec. 7, 1999

[54] SYSTEM AND METHOD OF EXTRACORPOREALLY TREATING BLOOD TO ALLEVIATE THE SYMPTOMS OF INFLAMMATORY DISEASES

[75] Inventors: Mitsuyo Sekiguchi, Yokohama; Yoshinori Takenaka, Souka, both of Japan

[73] Assignee: Asahi Medical Co., Ltd., Tokyo, Japan

[21] Appl. No.: 08/983,304

[22] PCT Filed: Jul. 10, 1996

[86] PCT No.: PCT/JP96/01913

§ 371 Date: Dec. 30, 1997

§ 102(e) Date: Dec. 30, 1997

[87] PCT Pub. No.: WO97/02851

PCT Pub. Date: Jan. 30, 1997

[30] Foreign Application Priority Data

Jul. 10, 1995 [JP] Japan .................................... 7-195754

[51] Int. Cl.⁶ ................................................. A61M 37/00
[52] U.S. Cl. ........................................ 604/4; 604/5; 604/6
[58] Field of Search .................................. 604/4, 5, 6, 7, 604/403, 406; 424/529, 532, 534

[56] References Cited

U.S. PATENT DOCUMENTS

| | | | |
|---|---|---|---|
| 4,828,543 | 5/1989 | Weiss et al. | 604/4 |
| 5,122,112 | 6/1992 | Jones | 604/4 |
| 5,362,406 | 11/1994 | Gsell et al. | 210/4 |
| 5,436,222 | 7/1995 | Kuna et al. | 514/12 |
| 5,437,861 | 8/1995 | Okarma et al. | 424/78.08 |
| 5,523,096 | 6/1996 | Okarma et al. | 424/489 |
| 5,707,622 | 6/1998 | Fong et al. | 424/145.1 |
| 5,730,713 | 3/1998 | Okarma et al. | 604/6 |
| 5,733,254 | 3/1998 | Jones et al. | 604/2 |
| 5,744,047 | 4/1998 | Gsell et al. | 210/767 |
| 5,762,805 | 6/1998 | Truitt et al. | 210/645 |
| 5,782,792 | 7/1998 | Jones et al. | 604/5 |
| 5,910,252 | 6/1999 | Truitt et al. | 210/645 |

FOREIGN PATENT DOCUMENTS 0 478 914 4/1992 European Pat. Off. .

OTHER PUBLICATIONS

Takefumi Kondoh et al., "Evaluation of a Filtration Lymphocytapheresis (LCP) Device for Use in the Treatment of Patients with Rheumatoid Arthritis", pp. 180–188, International Society for Artificial Organs, vol, 15. No. 3, 1991.

*Primary Examiner*—John G. Weiss
*Assistant Examiner*—Joseph F. Weiss, Jr.
*Attorney, Agent, or Firm*—Young & Thompson

[57] ABSTRACT

An extracorporeal blood circulation system for treating inflammatory diseases includes a blood collection device for collecting blood from a patient suffering from an inflammatory disease, an anticoagulant mixing device for mixing an anticoagulant into the collected blood, blood transportation device for transporting the anticoagulant-containing blood at a flow rate in the range of from 20 to 200 ml/minute, a blood treating device having a blood inlet and a blood outlet and containing a platelet activating device, and a blood returning device for returning the treated blood to the patient, each being liquid-tightly connected in this order through a tubing so that when extracorporeal blood circulation is conducted using the system with respect to blood from the patient, the system is capable of providing treated blood satisfying at least one requirement selected from requirement (1) of having a $\beta$-thromboglobulin concentration in the range of from 1,000 to 20,000 ng/ml and requirement (2) of having a platelet factor 4 concentration in the range of from 500 to 10,000 ng/ml. Also disclosed is an extracorporeal blood circulation method which provides treated blood in which platelets are activated to a specific degree that the abovementioned requirement (1) and/or requirement (2) is satisfied and so as to achieve a high therapeutic effect on inflammatory diseases.

6 Claims, 1 Drawing Sheet

FIG.1

SYSTEM AND METHOD OF EXTRACORPOREALLY TREATING BLOOD TO ALLEVIATE THE SYMPTOMS OF INFLAMMATORY DISEASES

BACKGROUND OF THE INVENTION

1. Field of the Invention

The present invention relates to an extracorporeal blood circulation system for treating inflammatory diseases. More particularly, the present invention is concerned with an extracorporeal blood circulation system for treating inflammatory diseases, which has a construction such that, when extracorporeal blood circulation is conducted using the system with respect to blood from a patient, the system is capable of providing treated blood in which platelets are activated to a specific degree. By the use of the extracorporeal blood circulation system of the present invention, a high therapeutic effect on inflammatory diseases can be achieved, as compared to a therapeutic effect achieved by conventional extracorporeal blood circulation therapies (such as plasmapheresis and a method using a leukocyte trapping filter).

2. Prior Art

An inflammatory disease is a disease in which an infiltration of leukocytes into a diseased site occurs, or a disease in which an inflammation markedly occurs due to active oxygen and various cytokines which are released from leukocytes.

Ulcerative colitis and Crohn's disease are chronic inflammatory diseases of the digestive tract. Currently, ulcerative colitis is generally believed to be a cryptogenic disease; however, it has been suspected that ulcerative colitis is attributable to an antilarge intestine antibody, an autoimmune T cell and the like.

Methods for treating these diseases can be classified into internal-medical treatment and surgical treatment. In an internal-medical treatment, drugs are used for the treatment, wherein such drugs are appropriately selected in accordance with the degree of seriousness of the symptoms and the location of the ulcer. Examples of such drugs include salazosulfapyridine (manufactured and sold by The Green Cross Corporation, Japan), prednisolone (manufactured and sold by Shionogi & Co., Ltd., Japan), azathioprine (manufactured and sold by Sumitomo Pharmaceuticals Co., Ltd., Japan and Nippon Wellcome K. K., Japan) and tranilast (manufactured and sold by KISSEI PHARMACEUTICAL CO., LTD., Japan). Such internal-medical treatments are effective for most cases of ulcerative colitis; however, the use of a drug for treating ulcerative colitis poses the danger of the occurrence of a side effect.

In a surgical treatment, excision of the diseased site is performed by a surgical operation. However, with respect to Crohn's disease, after the excision, the probability of the recurrence of the disease is high. Further, with respect to both of ulcerative colitis and Crohn's disease, after the excision, it is frequently necessary that the patient be fitted with an artificial anus, inevitably leading to a lowering of the quality of life (QOL).

Articular rheumatism is a cryptogenic generalized inflammatory disease in which the cardinal symptom is polyarthritis, and which may also exhibit various extra-articular symptoms, such as subcutaneous nodule, angiitis, pleurisy and diffuse interstitial pneumonia. It has been known that an autoantibody, which is called a rheumatoid factor, is present in serum and synovia from a patient suffering from articular rheumatism.

For treating this disease (articular rheumatism), various drugs are used in combination, wherein such drugs are selected from, for example, a non-steroidal anti-inflammatory drug, a steroidal drug, an immunosuppressant and an immunomodulator. A treatment using drugs is effective for most patients suffering from articular rheumatism; however, this treatment poses the danger of the occurrence of a side effect. With respect to inflammatory diseases which do not favorably respond to any drug or which cannot be treated with drugs due to serious side effects of the drugs, it has been reported that such inflammatory diseases have been effectively treated by using plasmapheresis, such as double filtration plasmapheresis and immunoadsorption plasmapheresis. Plasmapheresis is a therapeutic method in which a rheumatoid factor and an immune complex, both which are thought to be causative of inflammation, are removed from the patient. {With respect to plasmapheresis, reference can be made to, for example, the following literature: Y. Itakura et al., Effects of Double Filtration Plasmapheresis for Rheumatoid Arthritis, p.133–136, Therapeutic Plasmapheresis (VII), Proceedings of the Seventh Symposium on Therapeutic Plasmapheresis, Tokyo, Jun. 5–6, 1987, Japanese Society for Therapeutic Plasmapheresis; N. Kobayashi et al., Plasma Cleaning Using Immunoadsorbent IM-P for Patients with Rheumatoid Arthritis, p.153–157, Therapeutic Plasmapheresis (IV), Proceedings of the 4th Symposium on Therapeutic Plasmapheresis, Tokyo, Jun. 2nd, 1984, Japanese Society for Therapeutic Plasmapheresis. } However, the convntional techniques of plasmapheresis are unsatisfactory in therapeutic effect. It is desired to improve the therapeutic effect of plasmapheresis.

In recent years, it has been suggested that inflammatory diseases (such as ulcerative colitis and articular rheumatism) can be treated by reducing the number of leukocytes present in the blood of a patient, using a device comprising a fibrous filter (see European Patent Application Publication No. 478,914, Pall Corporation). Further, there is also a report that, when a patient suffering from articular rheumatism was subjected to a lymphocyte removal therapy, the symptoms of the patient were alleviated (Artificial Organs, Vol. 15, No. 3, 1991).

However, the alleviation of clinical symptoms accompanying inflammatory diseases, which can be achieved by an extracorporeal blood circulation using a known leukocyte trapping filter, is at best similar to that obtained by plasmapheresis. Therefore, it is desired to improve the therapeutic effect of the extracorporeal blood circulation therapy.

SUMMARY OF THE INVENTION

In this situation, the present inventors have made extensive and intensive studies with a view toward developing a method for treating inflammatory diseases, which can achieve a high therapeutic effect, as compared to a therpeutic effect achieved by the conventional therapeutic methods. As a result, the following has unexpectedly been found. Conventionally, in performing a therapeutic method in which blood is taken out of the body of a patient and the blood is treated and then returned to the body of the patient (i.e., in performing an extracorporeal blood circulation therapy), it has been an established knowledge that, as materials for equipment used in the therapy (e.g., a material for a tubing used for extracorporeal blood circulation and a material for a blood treating element), use should be made of those materials which are as excellent as possible in the ability to avoid activation of the coagulation system (including platelets), the complement system and the like with respect to the blood. However, in connection with the therapy of inflammatory diseases, the present inventors have made a quite surprising finding which overturns such conventional knowledge in the field of the extracorporeal blood circulation methods for treating diseases. Specifically, the present inventors have found that, in an extracorporeal blood circulation method for treating inflammatory diseases, a high therapeutic effect can be achieved by activating platelets in the extracorporeally circulated blood to a degree that treated blood satisfies at least one requirement selected from the group consisting of the following requirements (1) and (2):

(1) having a β-thromboglobulin concentration in the range of from 1,000 to 20,000 ng/ml, as measured just outside of a blood outlet of blood treating means; and (2) having a platelet factor 4 concentration in the range of from 500 to 10,000 ng/ml, as measured just outside of a blood outlet of blood treating means.

The present invention has been completed, based on the above novel finding.

Accordingly, it is an object of the present invention to provide an extracorporeal blood circulation system for treating inflammatory diseases, which is capable of providing treated blood in which platelets are activated to a specific degree, thereby achieving a high therapeutic effect on inflammatory diseases, as compared to a therapeutic effect achieved by conventional extracorporeal blood circulation systems for treating inflammatory diseases.

It is another object of the present invention to provide an extracorporeal blood circulation method for treating inflammatory diseases, which is capable of providing treated blood in which platelets are activated to a specific degree, thereby achieving a high therapeutic effect on inflammatory diseases, as compared to a therapeutic effect achieved by conventional extracorporeal blood circulation methods for treating inflammatory diseases.

The foregoing and other objects, features and advantages of the present invention will be apparent from the following detailed description taken in connection with the accompanying drawing and the appended claims.

BRIEF DESCRIPTION OF THE DRAWING

In the drawing:

FIG. 1. is a diagram showing an example of the extracorporeal blood circulation system of the present invention. Description of the reference numerals:
1: Means for collecting blood from a patient
2: Means for mixing an anticoagulant into the collected blood
2A: Anticoagulant
3: Means for transporting the anticoagulant-containing blood
4: Blood treating means containing platelet activating means
4A: Platelet activating means
5: Means for returning the treated blood to the patient
6: Microaggregate trapping means
6A: Arterial pressure monitor
7: Drip chamber
7A: Venous pressure monitor

DETAILED DESCRIPTION OF THE INVENTION

In one aspect of the present invention, there is provided an extracorporeal blood circulation system for treating inflammatory diseases, comprising:

blood collection means for collecting blood from a patient suffering from an inflammatory disease, anticoagulant mixing means for mixing an anticoagulant into the collected blood, the anticoagulant having the ability to suppress an increase in concentration of at least one platelet factor in the collected blood, the at least one platelet factor being selected from the group consisting of β-thromboglobulin and platelet factor 4, blood transportation means for transporting the anticoagulant-containing blood at a flow rate in the range of from 20 to 200 ml/minute, blood treating means having a blood inlet and a blood outlet and containing platelet activating means having the ability to increase, upon treatment of blood with the blood treating means, the concentration of the at least one platelet factor in the blood, and blood returning means for returning the treated blood to the patient, the blood collection means, the anticoagulant mixing means, the blood transportation means, the blood treating means and the blood returning means being liquid-tightly connected in this order through a tubing, wherein, when extracorporeal blood circulation is conducted using the system with respect to blood from the patient, the system is capable of providing treated blood satisfying at least one requirement selected from the group consisting of the following requirements (1) and (2):

(1) having a β-thromboglobulin concentration in the range of from 1,000 to 20,000 ng/ml, as measured just outside of the blood outlet of the blood treating means; and (2) having a platelet factor 4 concentration in the range of from 500 to 10,000 ng/ml, as measured just outside of the blood outlet of the blood treating means.

In another aspect of the present invention, there is provided an extracorporeal blood circulation method for treating inflammatory diseases, comprising:

collecting blood from a patient suffering from an inflammatory disease, mixing an anticoagulant into the collected blood, the anticoagulant having the ability to suppress an increase in concentration of at least one platelet factor in the collected blood, the at least one platelet factor being selected from the group consisting of β-thromboglobulin and platelet factor 4, transporting the blood having the anticoagulant mixed thereinto at a flow rate in the range of from 20 to 200 ml/minute to blood treating means having a blood inlet and a blood outlet and containing platelet activating means having the ability to increase, upon treatment of blood with the blood treating means, the concentration of the at least one platelet factor in the blood, passing the blood through the blood treating means from the inlet to the outlet to treat the blood, and returning the treated blood to the patient, the treated blood satisfying at least one requirement selected from the group consisting of the following requirements (1) and (2):

(1) having a β-thromboglobulin concentration in the range of from 1,000 to 20,000 ng/ml, as measured just outside of the blood outlet of the blood treating means; and (2) having a platelet factor 4 concentration in the range of from 500 to 10,000 ng/ml, as measured just outside of the blood outlet of the blood treating means.

For an easy understanding of the present invention, the essential features and various preferred embodiments of the present invention are enumerated below.

1. An extracorporeal blood circulation system for treating inflammatory diseases, comprising:

blood collection means for collecting blood from a patient suffering from an inflammatory disease, anticoagulant mixing means for mixing an anticoagulant into the collected blood, the anticoagulant having the ability to suppress an increase in concentration of at least one platelet factor in the collected blood, the at least one platelet factor being selected from the group consisting of β-thromboglobulin and platelet factor 4, blood transportation means for transporting the anticoagulant-containing blood at a flow rate in the range of from 20 to 200 ml/minute, blood treating means having a blood inlet and a blood outlet and containing platelet activating means having the ability to increase, upon treatment of blood with the blood treating means, the concentration of the at least one platelet factor in the blood, and blood returning means for returning the treated blood to the patient, the blood collection means, the anticoagulant mixing means, the blood transportation means, the blood treating means and the blood returning means being liquid-tightly connected in this order through a tubing, wherein, when extracorporeal blood circulation is conducted using the system with respect to blood from the patient, the system is capable of providing treated blood satisfying at least one requirement selected from the group consisting of the following requirements (1) and (2):

(1) having a β-thromboglobulin concentration in the range of from 1,000 to 20,000 ng/ml, as measured just outside of the blood outlet of the blood treating means; and (2) having a platelet factor 4 concentration in the range of from 500 to 10,000 ng/ml, as measured just outside of the blood outlet of the blood treating means.

2. The extracorporeal blood circulation system according to item 1 above, wherein the blood treating means is a module comprising a casing having a blood inlet and a blood outlet, and said platelet activating means packed therein, the platelet activating means comprising a material comprised mainly of at least one member selected from the group consisting of fibers, a porous material, particles, a film, a planar membrane, a hollow fiber membrane and a tubular material.

3. The extracorporeal blood circulation system according to item 1 above, wherein the blood treating means has a pressure drop index in the range of from 20 to 150, wherein the pressure drop index is defined as a value obtained by a method in which heparin is added to bovine blood having a hematocrit value of about 40% and a total protein of about 6.5 g/dl of plasma so that a final heparin concentration becomes 5 units (in accordance with the meaning of a unit as defined in the 12th Revised Japanese Pharmacopeia) per ml of the bovine blood; the bovine blood is flowed through the blood treating means at a flow rate of 50 ml/minute, wherein, before the bovine blood enters the blood treating means, the same anticoagulant as used in a treatment of the patient with the extracorporeal blood circulation system is mixed into the bovine blood in the same manner as in the treatment of the patient; a blood pressure difference (mmHg) as between the blood inlet and blood outlet of the blood treating means is measured 20 minutes after the start of the flowing of the bovine blood; and the blood pressure difference is taken as a pressure drop index.

4. The extracorporeal blood circulation system according to item 1 above, wherein the platelet activating means is capable of removing leukocytes.

5. An extracorporeal blood circulation method for treating inflammatory diseases, comprising:

collecting blood from a patient suffering from an inflammatory disease, mixing an anticoagulant into the collected blood, the anticoagulant having the ability to suppress an increase in concentration of at least one platelet factor in the collected blood, the at least one platelet factor being selected from the group consisting of β-thromboglobulin and platelet factor 4, transporting the blood having the anticoagulant mixed thereinto at a flow rate in the range of from 20 to 200 ml/minute to blood treating means having a blood inlet and a blood outlet and containing platelet activating means having the ability to increase, upon treatment of blood with the blood treating means, the concentration of the at least one platelet factor in the blood, passing the blood through the blood treating means from the inlet to the outlet to treat the blood, and returning the treated blood to the patient, the treated blood satisfying at least one requirement selected from the group consisting of the following requirements (1) and (2):

(1) having a β-thromboglobulin concentration in the range of from 1,000 to 20,000 ng/ml, as measured just outside of the blood outlet of the blood treating means; and (2) having a platelet factor 4 concentration in the range of from 500 to 10,000 ng/ml, as measured just outside of the blood outlet of the blood treating means.

6. The extracorporeal blood circulation method according to item 5 above, wherein the blood treating means is a module comprising a casing having a blood inlet and a blood outlet, and said platelet activating means packed therein, the platelet activating means comprising a material comprised mainly of at least one member selected from the group consisting of fibers, a porous material, particles, a film, a planar membrane, a hollow fiber membrane and a tubular material.

7. The extracorporeal blood circulation method according to item 5 above, wherein the blood treating means has a pressure drop index in the range of from 20 to 150, wherein the pressure drop index is defined as a value obtained by a method in which heparin is added to bovine blood having a hematocrit value of about 40% and a total protein of about 6.5 g/dl of plasma so that a final heparin concentration becomes 5 units (in accordance with the meaning of a unit as defined in the 12th Revised Japanese Pharmacopeia) per ml of the bovine blood; the bovine blood is flowed through the blood treating means at a flow rate of 50 ml/minute, wherein, before the bovine blood enters the blood treating means, the same anticoagulant as used in a treatment of the patient with the extracorporeal blood circulation system is mixed into the bovine blood in the same manner as in the treatment of the patient; a blood pressure difference (mmHg) as between the blood inlet and blood outlet of the blood treating means is measured 20 minutes after the start of the flowing of the bovine blood; and the blood pressure difference is taken as a pressure drop index.

8. The extracorporeal blood circulation method according to item 5 above, wherein the platelet activating means is capable of removing leukocytes.

Hereinbelow, the present invention will be explained in more detail with reference to FIG. 1.

Figure 1:
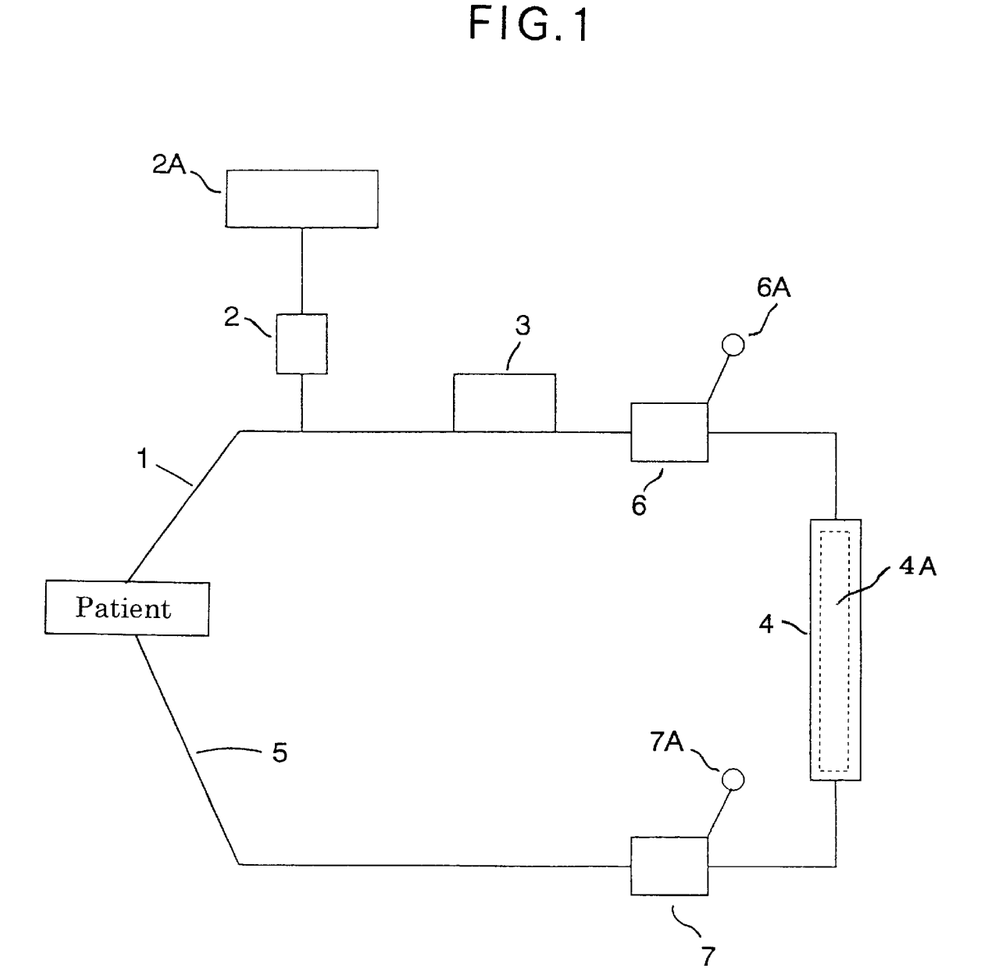

FIG. 1 is a diagram showing an example of the extracorporeal blood circulation system of the present invention. The extracorporeal blood circulation system shown in FIG. 1 comprises means 1 for collecting blood from a patient suffering from an inflammatory disease, means 2 for mixing anticoagulant 2A with the collected blood, means 3 for transporting the anticoagulant-containing blood at a flow rate in the range of from 20 to 200 ml/minute, microaggregate trapping means 6 having arterial pressure monitor 6A, blood treating means 4 having a blood inlet and a blood outlet and containing platelet activating means 4A, drip chamber 7 having venous pressure monitor 7A and means 5 for returning the treated blood to the patient are liquid-tightly connected in this order through a tubing. Examples of means 1 for collecting blood from a patient suffering from an inflammatory disease include a needle and a catheter which are used in known extracorporeal blood circulation apparatuses. As an example of blood transportation means 3, there can be mentioned a blood transportation pump (such as a peristaltic pump) used in a known extracorporeal blood circulation apparatus. When such a known blood transportation pump is used as blood transportation means 3 of the extracorporeal blood circulation system, it is preferred that a tubing used in the pump has a relatively small inner diameter, from the viewpoint of preventing the blood entering the platelet activating means from assuming a pulsating flow. The flow rate for the blood transportation is appropriately selected in the range of from 20 to 200 ml/minute, wherein the selected flow rate is desired to be, for example, a value such that the burden of the flow rate on the patient is as small as possible in respect of both the blood collection and blood return, and that clogging of, e.g., the blood treating means with microaggregates does not occur.

As an example of means 2 for mixing anticoagulant 2A into the collected blood, there can be mentioned a known infusion pump which can feed into the collected blood an anticoagulant stored in a container. When a low molecular weight heparin or the like is used as the anticoagulant, the means for mixing an anticoagulant into the collected blood may be a device which can be used for directly feeding into the collected blood an anticoagulant without using a pump. The feeding of an anticoagulant into the collected blood may also be performed by using a pressure head, instead of a pump. Further, when a drip chamber as mentioned below is used in the blood circulation system, it is preferred that the anticoagulant is fed into the collected blood at a position in the system on a side upstream of the drip chamber, as viewed in the flow direction of the collected blood. When the anticoagulant is fed into the collected blood at a position in the system on a side upstream of the drip chamber, the resultant mixture of the anticoagulant and the blood is temporarily pooled in the drip chamber, so that a more improved mixing of the anticoagulant into the blood can be achieved, leading to a reduction in a danger such that blood coagulation causes a clogging of the platelet activating means contained in the blood treating means positioned downstream of the drip chamber. It is also preferred that drip chamber 7 equipped with a mesh is provided downstream of blood treating means 4, as shown in FIG. 1.

Generally, in the extracorporeal blood circulation therapies, as anticoagulant, use is made of Acid-Citrate-Dextrose A solution (hereinafter, frequently referred to simply as "ACD-A solution"), heparin (including a low molecular weight heparin), nafamostat mesilate, gabexate mesilate or the like. In the present invention, any of these known anticoagulants can be used. An ACD-A solution is generally used in an amount such that the (anticoagulant/blood) volume ratio falls in the range of from 1:15 to 1:5. Anticoagulants other than ACD-A solution are used in an amount such that the (anticoagulant/blood) volume ratio falls in the range of from about 1:3,000 to about 1:1,000. Thus, in the case of the use of anticoagulants other than ACD-A solution, the proportion of blood in the total volume of the anticoagulant and blood is very high, so that it is not easy to achieve a satisfactory mixing between the anticoagulant and blood. Therefore, for achieving a better mixing of an anticoagulant other than ACD-A solution into blood, a method may be employed in which an anticoagulant other than ACD-A solution is preliminarily diluted with a physiological solution and then, the diluted anticoagulant is continuously fed into the blood during the extracorporeal blood circulation. With respect to the amount of a physiological solution used for diluting the anticoagulant (in order to achieve a better mixing of the anticoagulant into blood), the amount of a physiological solution is appropriately chosen, taking into consideration a balance between the suppression of the occurrence of clogging in the system and the prevention of a heavy burden on the patient due to the introduction of too large an amount of a physiological solution into the patient. In general, it is preferred that the anticoagulant is diluted 100-fold to 300-fold with a physiological solution. As examples of physiological solutions, there can be mentioned a physiological saline exhibiting an osmotic pressure of from 200 to 400 mOsm, preferably from 280 to 300 mOsm, and a 5 w/v % (5 g/dl) aqueous glucose solution.

In the present invention, with respect to the structure of blood treatment means 4 having a blood inlet and a blood outlet and containing platelet activating means 4A having the ability to increase, upon treatment of blood with the blood treating means, the concentration of the above-mentioned at least one platelet factor in the blood, there is no particular limitation. However, not preferred is a structure which significantly activates blood coagulation factors other than β-thromboglobulin and platelet factor 4, leading to the occurrence of coagulation of the treated blood. As mentioned below, examples of blood treating means containing platelet activating means, which are employable in the present invention, include a module comprising a casing having a blood inlet and a blood outlet, and platelet activating means packed therein, wherein the platelet activating means comprises a material comprised mainly of at least one member selected from the group consisting of fibers, a porous material, particles, a film, a planar membrane, a hollow fiber membrane and a tubular material.

When extracorporeal blood circulation is conducted using the extracorporeal blood circulation system of the present invention, the system is so constructed as is capable of providing treated blood satisfying at least one requirement selected from the group consisting of the following requirements (1) and (2):

(1) having a β-thromboglobulin concentration in the range of from 1,000 to 20,000 ng/ml, as measured just outside of the blood outlet of the blood treating means after about 1.5 litters of blood has been treated by the system from the start of the extracorporeal blood circulation; and (2) having a platelet factor 4 concentration in the range of from 500 to 10,000 ng/ml, as measured just outside of the blood outlet of the blood treating means after about 1.5 litters of blood has been treated by the system from the start of the extracorporeal blood circulation.

A platelet has a platelet granule therein, and the platelet granule contains platelet factor 4, β-thromboglobulin, serotonin and the like. When a platelet is activated by some stimulation, it undergoes a release reaction which causes the above-mentioned substances contained in the platelet granule to be released out of the platelet. With respect to the function of platelet factor 4, it is known that platelet factor 4 specifically binds to heparin to neutralize the anticoagulation activity of heparin. With respect to the function of β-thromboglobulin, it is known that β-thromboglobulin has an antagonistic activity against urokinase. Urokinase is one of plasminogen activators, which activate plasminogen to induce conversion of plasminogen into plasmin which has a thrombolysis activity. Accordingly, β-thromboglobulin inhibits thrombolysis due to its antagonism against urokinase.

With respect to the mechanism of the unexpected phenomenon that, in an extracorporeal blood circulation method for treating inflammatory diseases, a high therapeutic effect can be achieved by activating platelets in the extracorporeally circulated blood to a specific degree, complete elucidation of the mechanism of this unexpected phenomenon, which overturns conventional knowledge in the art, has not yet been made. However, it is presumed that, by activating platelets to a specific degree, neutrophile chemotactic factors (such as platelet factor 4) are released from platelets, and the released neutrophile chemotactic factors cause neutrophiles to wander out of the inflamed site to thereby reduce the neutrophile concentration at and around the inflamed site, leading to the suppression of the inflammation.

In the blood of a healthy person, the β-thromboglobulin concentration is about 20 to about 40 ng/ml and the platelet factor 4 concentration is about 7 to about 20 ng/ml. Therefore, when the β-thromboglobulin concentration does not reach 1,000 ng/ml and/or the platelet factor 4 concentration does not reach 500 ng/ml, it means that platelets in the blood are in a slightly activated state, as compared to platelets in the blood of a healthy person; however, since these concentration values are lower than the respective ranges of the above-mentioned requirements (1) and (2) defined in the present invention, the excellent therapeutic effects of the present invention cannot be achieved. Specifically, with respect to a patient suffering from an inflammatory disease, when both the β-thromboglobulin concentration and the platelet factor 4 concentration are lower than the respective ranges of the above-mentioned requirements (1) and (2) defined in the present invention, it is expected that the amount of neutrophile chemotactic factors released from platelets is unsatisfactorily small, wherein examples of neutrophile chemotactic factors include platelet factor 4, 12-L-hydroxy-5,8,10,14-eicosatetraenoic acid and 12-L-hydroxy-5,8,10-heptadecatrienoic acid. Therefore, in this case, a lowering of the neutrophile concentration at or around an inflamed site dose not occur, so that the excellent effects of the present invention cannot be exhibited, that is, a high degree of alleviation of the clinical symptoms of an inflammatory disease cannot be expected. On the other hand, when treated blood has too high a β-thromboglobulin concentration and too high a platelet factor 4 concentration, blood coagulation is likely to proceed, so that the blood circulation system is clogged with coagulated blood and it becomes impossible to use the blood circulation system. Therefore, in the extracorporeal blood circulation system of the present invention, it is requisite that the system be constructed so as to be capable of providing treated blood satisfying at least one requirement selected from the group consisting of requirement (1) of having a β-thromboglobulin concentration in the range of from 1,000 to 20,000 ng/ml, as measured just outside of the blood outlet of the blood treating means, and requirement (2) of having a platelet factor 4 concentration in the range of from 500 to 10,000 ng/ml, as measured just outside of the blood outlet of the blood treating means.

It is preferred that the β-thromboglobulin concentration is in the range of from 1,500 to 20,000 ng/ml, more preferably from 2,000 to 20,000 ng/ml, most preferably from 3,000 to 20,000 ng/ml.

It is preferred that the platelet factor 4 concentration is in the range of from 750 to 10,000 ng/ml, more preferably from 900 to 10,000 ng/ml, most preferably from 1,500 to 10,000 ng/ml.

For achieving the excellent effects of the present invention, it is necessary to activate platelets to a degree that at least one of the above-mentioned β-thromboglobulin concentration requirement (1) and the platelet factor 4 concentration requirement (2) is satisfied, and it is not necessary that both of the β-thromboglobulin concentration requirement (1) and the platelet factor 4 concentration requirement (2) are satisfied. However, in general, when platelets are activated, there is a tendency that the β-thromboglobulin concentration and platelet factor 4 concentration are simultaneously elevated.

In the present invention, each of the β-thromboglobulin concentration and platelet factor 4 concentration is measured with respect to a blood sample taken at a position in the system just outside of the blood outlet of the blood treating means. Each of these concentration values can be measured by, for example, enzyme immunoassay (hereinafter, frequently referred to simply as "EIA").

In the present invention, platelets present in the collected blood are activated to a specific degree that the above-mentioned requirement (1) and/or requirement (2) is satisfied. The activation of platelets to such a specific degree can be achieved as a total effect of both of:

anticoagulant 2A having the ability to suppress an increase in concentration of at least one platelet factor in the collected blood, wherein the above-mentioned at least one platelet factor is selected from the group consisting of β-thromboglobulin and platelet factor 4, and blood treating means 4 containing platelet activating means having the ability to increase, upon treatment of blood with the blood treating means, the concentration of the above-mentioned at least one platelet factor in the blood.

With respect to the structure of the blood treating means, there is no particular limitation as long as platelets can be activated to a specific degree that the above-mentioned requirement (1) and/or requirement (2) is satisfied. In the present invention, as a preferred example of blood treating means, there can be mentioned a module comprising a casing having a blood inlet and a blood outlet, and platelet activating means packed therein, wherein the platelet activating means comprises a material comprised mainly of at least one member selected from the group consisting of fibers, a porous material, particles, a film, a planar membrane, a hollow fiber membrane and a tubular material. Specific examples of the above-mentioned module include:

a module comprising a casing and, packed therein, a depth filter which is comprised of a fibrous or porous material having narrow gaps through which blood can pass;

a module comprising a column and, packed therein, particles, beads or the like; and a module comprising a casing and, packed therein, a bundle of porous hollow fiber membranes.

Examples of materials for the above-mentioned fibers, particles and film include a polyester, polypropylene, a polyamide, polyethylene, polyacrylonitrile, cellulose acetate, polystyrene, a polysulfone, a glass and a ceramic. Examples of materials for the above-mentioned planar membrane and hollow fiber membrane include polyacrylonitrile, cellulose acetate, polymethyl methacrylate, a polysulfone, cellulose and ethylene vinyl alcohol. Examples of materials for the above-mentioned tubular material include polyvinyl chloride, a silicone rubber and a polyurethane. Examples of materials for the above-mentioned porous material include a polyurethane, a polyester and polyvinyl formal.

Further, as a simple form of the platelet activating means, there can be mentioned the inner wall of a portion of the extracorporeal blood circulation circuit structure (at such a portion of the circuit structure, the inner wall is contacted by the blood during the extracorporeal blood circulation), wherein the inner wall has been modified into a material or condition which is capable of activating platelets. Examples of methods for the modification of the inner wall of such a portion of the extracorporeal blood circulation circuit structure into a material which is capable of activating platelets include a method in which a hydrophobic property is imparted to the surface of the inner wall, and a method in which a positive electric charge is imparted to the surface of the inner wall. On the other hand, as an example of methods for the modification of the inner wall into a condition which is capable of activating platelets, there can be mentioned a method in which the surface of the inner wall is roughened.

With respect to the manner of using an anticoagulant in the extracorporeal blood circulation method of the present invention for treating inflammatory diseases, there is no particular limitation as long as platelets can be activated to a specific degree that the above-mentioned requirement (1) and/or requirement (2) is satisfied. For example, when 3 liters of blood is treated by extracorporeal blood circulation, the following methods for mixing an anticoagulant into blood can be used. The methods include a method in which nafamostat mesilate is solely used as the anticoagulant, wherein nafamostat mesilate is continuously fed at a feeding rate of from 10 to 30 mg/hour; a method in which heparin is solely used as the anticoagulant, wherein heparin is first fed as a single shot in an amount of from 500 to 3,000 units and then is continuously fed at a feeding rate of from 500 to 2,000 units/hour; a method in which heparin and nafamostat mesilate are used in combination as the anticoagulant, wherein heparin is first fed as a single shot in an amount of from 500 to 3,000 units and then is continuously fed at a feeding rate of from 500 to 2,000 units/hour while continuously feeding nafamostat mesilate at a feeding rate of from 1 to 50 mg/hour; a method in which heparin and gabexate mesilate are used in combination as the anticoagulant, wherein heparin is first fed as a single shot in an amount of from 500 to 3,000 units and then is continuously fed at a feeding rate of from 500 to 2,000 units/hour while continuously feeding gabexate mesilate at a feeding rate of from 500 to 3,000 mg/hour; and a method in which an ACD-A solution is solely used as the anticoagulant, wherein the ACD-A solution is continuously fed at a feeding rate corresponding to $1/10$ to $1/16$ of the flow rate of the collected blood. In the present invention, the term "unit" used for expressing an amount of heparin means a unit as defined in the 12th Revised Japanese Pharmacopeia.

When the blood treating means used in the present invention has a pressure drop index in the range of from 20 to 150, wherein the pressure drop index is as defined above, it becomes extremely easy to provide treated blood which satisfies at least one requirement selected from the group consisting of the above-mentioned requirements (1) and (2), namely, requirement (1) of having a β-thromboglobulin concentration in the range of from 1,000 to 20,000 ng/ml, as measured just outside of the blood outlet of the blood treating means, and requirement (2) of having a platelet factor 4 concentration in the range of from 500 to 10,000 ng/ml, as measured just outside of the blood outlet of the blood treating means. It is preferred that the pressure drop index is in the range of from 35 to 150, more preferably from 50 to 150, still more preferably from 60 to 150. When the pressure drop index of the blood treating means is less than 20, platelets cannot be activated to a satisfactory degree and it is highly likely that any of the above-mentioned requirements (1) and (2) cannot be satisfied, so that a desired therapeutic effect is almost not able to be achieved. Further, when the pressure drop index of the blood treating means is more than 150, it is likely that platelets are activated to too great a degree, thus disadvantageously causing the coagulation system of blood to be fully activated, so that the blood circulation system is clogged with coagulated blood.

In the present invention, when platelets are activated to the above-mentioned specific degree while removing leukocytes contained in the collected blood to some extent, the therapeutic effect on inflammatory diseases can be further increased. Therefore, it is preferred that, in addition to blood treating means 4 containing platelet activating means, the extracorporeal blood circulation system of the present invention contains a known leukocyte trapping filter comprising a material comprised mainly of fibers, a porous material or the like. As an example of a known leukocyte trapping filter, there can be mentioned a filter disclosed in European Patent Application Publication No. 478914 (corresponding to U.S. Pat. No. 5,362,406).

Further, it is more preferred that the platelet activating means 4A of blood treating means 4 is also capable of removing leukocytes. This is because, by using platelet activating means 4A also capable of removing leukocytes, the amount of blood which is being extracorporeally circulated can be decreased, as compared to that in the case of using a separate leukocyte trapping filter as mentioned above which is incorporated into the system in addition to blood treating means 4 containing platelet activating means 4A.

It is especially preferred that the platelet activating means specifically captures leukocytes from blood and is not likely to capture erythrocytes and useful protein components of plasma. Preferred specific examples of blood treating means 4 containing such platelet activating means include:

a module comprising a casing having a blood inlet and a blood outlet, and platelet activating means packed therein at a density of from 0.05 to 0.5 g/cm$^3$, wherein the platelet activating means comprises a filter medium comprised mainly of a fiber mass, a non-woven fabric or the like having an average fiber diameter of from about 1 to about 10 μm;

a module comprising a casing having a blood inlet and a blood outlet, and platelet activating means packed therein, wherein the platelet activating means comprises a filter medium comprised mainly of a porous material having an average pore diameter of from 3 to 50 μm; and a module comprising a casing having a blood inlet and a blood outlet, and platelet activating means packed therein, wherein the platelet activating means comprises a filter medium comprised of particles having a particle diameter of from 0.1 to 10 mm.

The blood treated by the blood treating means is returned to the patient through blood returning means 5 for returning the treated blood to the patient. Examples of blood returning means for returning the treated blood to the patient include those which are mentioned above as examples of the means for collecting blood from a patient.

Further, in the extracorporeal blood circulation system of the present invention, it is also preferred that microaggregate trapping means 6 for trapping microaggregates from the collected blood is provided between blood collection means 1 for collecting blood from a patient and blood returning means 5 for returning the treated blood to the patient.

With respect to the microaggregate trapping means, it need not be provided in the form of an independent device, such as a drip chamber which has provided therein a mesh capable of removing microaggregates from blood by filtration. The microaggregate trapping means may be provided, for example, in the form of a mesh or the like which is capable of trapping microaggregates and which is disposed in the blood treating means upstream of the platelet activating means, as viewed in the flow direction of the collected blood.

As mentioned above, in the present invention, as blood treating means 4 containing platelet activating means which is also capable of removing leukocytes from blood, use may be made of a module comprising a casing having a blood inlet and a blood outlet, and platelet activating means packed therein, wherein the platelet activating means comprises a filter medium comprised of a non-woven fabric. In this case, as a preferred example of such a filter medium, there can be mentioned a filter medium comprising a main filter comprised of a non-woven fabric having a small average fiber diameter of from 1.0 to 5.0 μm and a rough pre-filter having a large average fiber diameter of from 5 to 50 μm for trapping microaggregates from the collected blood, wherein the rough pre-filter is disposed upstream of the main filter, as viewed in the flow direction of the collected blood.

Further, as mentioned above and as shown in FIG. 1, it is also preferred that drip chamber 7 equipped with a mesh is provided downstream of blood treating means 4.

In addition, in the extracorporeal blood circulation system of the present invention, it is also preferred to use a plurality of blood treating means 4 arranged in parallel, or provide a bypass tubing so as to circumvent blood treating means 4. When a plurality of blood treating means 4 arranged in parallel are used, there is an advantage in that, by allowing one or some of the plurality of blood treating means to be left unused as a reserve, when any sign is observed wherein the treatment of the collected blood with blood treating means 4 causes excess activation of platelets and/or an activation of the entire blood coagulating system, the blood flow route can be changed immediately so that the body fluid is led solely into the reserved, fresh blood treating means, thereby enabling the platelet activating means of the malfunctioning blood treating means to be washed or regenerated without interrupting the extracorporeal blood circulation therapy. Likewise, when a bypass tubing which circumvents blood treating means 4 is provided, there is an advantage in that, when any sign of malfunctioning is observed with respect to blood treating means 4, the blood flow route can be changed immediately so that the body fluid is led solely into the bypass tubing, thereby enabling the platelet activating means of the malfunctioning blood treating means to be washed and regenerated while passing the body fluid through the bypass tubing.

BEST MODE FOR CARRYING OUT THE INVENTION

Hereinbelow, the present invention will be described in more detail with reference to the following Examples and Comparative Examples, which should not be construed as limiting the scope of the present invention.

In Examples and Comparative Examples as mentioned below, each of the β-thromboglobulin concentration in blood and the platelet factor 4 concentration in blood was measured by EIA.

With respect to the terms "tender joint score", "swollen joint score" and "Ritchie Index" which are mentioned below, each of these terms is well known in association with the methods for evaluating the condition of a patient suffering from articular rheumatism. With respect to the tender joint score and swollen joint score, reference can be made to Hamamoto et al., Medical Practice, Vol. 8, No. 7, p.1055–1059, 1991. With respect to Ritchie Index, reference can be made to Ritchie et al., Quarterly Journal of Medicine, New Series XXXVII, No. 147, p.393–406, July 1968.

EXAMPLE 1 AND COMPARATIVE EXAMPLE 1

In each of Example 1 and Comparative Example 1, for treating a patient suffering from ulcerative colitis, an extracorporeal blood circulation system as shown in FIG. 1 was prepared.

In Example 1, a non-woven fabric filter material sheet having an average fiber diameter of about 1.7 μm, a thickness of 0.30 mm and a bulk density of 0.20 g/cm$^3$ was spirally wound and laminated to form a cylindrical structure having a weight of 15 g and having a hollow portion extending between both ends, thus obtaining a filter having a weight of 15 g. The obtained filter was packed in a cylindrical casing having an inlet and an outlet and having an inner diameter of 45 mm and an internal-space length of 160 mm, to thereby obtain filter device (α). In Example 1, the thus obtained filter device (α) was used as blood treating means 4 containing platelet activating means also capable of removing leukocytes.

In Comparative Example 1, a non-woven fabric filter material sheet having an average fiber diameter of about 2.8 μm, a thickness of 0.42 mm and a bulk density of 0.21 g/cm$^3$ was spirally wound and laminated to form a cylindrical structure having a weight of 11 g and having a hollow portion extending between both ends, thus obtaining a cylindrical main filter having a weight of 11 g. Onto the peripheral surface of the obtained main filter was spirally wound and laminated a non-woven fabric filter material sheet having an average fiber diameter of about 12 μm, a thickness of 0.21 mm and a bulk density of 0.21 g/cm$^3$ to form an innermost pre-filter layer having a weight of 8 g. Then, onto the formed innermost pre-filter layer was spirally wound and laminated a non-woven fabric filter material sheet having an average fiber diameter of about 12 μm, a thickness of 0.47 mm and a bulk density of 0.14 g/cm$^3$ to form an intermediate pre-filter layer having a weight of 4 g. Next, onto the formed intermediate pre-filter layer was spirally wound and laminated a non-woven fabric filter material sheet having an average fiber diameter of about 33 μm, a thickness of 0.22 mm and a bulk density of 0.23 g/cm$^3$ to form an outermost pre-filter layer having a weight of 4 g. Thus, there was obtained a filter comprised of a main filter and three different pre-filters and having a weight of 27 g. The obtained filter was packed in a cylindrical casing having an inlet and an outlet and having an inner diameter of 45 mm and an internal-space length of 160 mm, to thereby obtain filter device (β). In Comparative Example 1, the thus obtained filter device (β) was used as blood treating means 4 containing platelet activating means 4A also capable of removing leukocytes.

In each of filter devices (α) and (β) prepared above, the blood inlet is positioned at one end of the casing, and the blood outlet is positioned at the other end of the casing. Each of filter devices (α) and (β) is so designed that blood enters the filter device through the blood inlet thereof and spreads over the outer peripheral surface of the cylindrical filter contained therein, and permeates into the interior of the filter to reach the inner peripheral surface of the filter, where the blood goes into the hollow portion and flows therethrough toward the blood outlet of the filter device, through which the blood goes out of the filter device. With respect to each of filter devices (α) and (β), the entire surface of an end of the cylindrical filter on a side of the blood inlet of the filter device was sealed so as to prevent blood from entering the filter through the end portion thereof.

Using individually the extracorporeal blood circulation systems in which the above-mentioned filter devices (α) and (β) are, respectively, incorporated as blood treating means 4, with respect to two patients suffering from ulcerative colitis, extracorporeal blood circulation for one hour at a flow rate of 50 ml/minute was performed five times at a frequency of once per week. As the anticoagulant, an ACD-A solution was continuously added to the collected blood at a rate of 300 ml/hour.

The leukocyte removing ability of the platelet activating means contained in the blood treating means was expressed in terms of a leukocyte removal ratio (%) which was measured by a method in which two blood samples are respectively taken, at positions upstream and downstream of the blood treating means as viewed in the flow direction of the collected blood, 30 minutes after the start of the extracorporeal blood circulation; the number of leukocytes contained in each of the two blood samples taken before and after the treatment of the blood with the blood treating means was counted to obtain two counts of leukocytes; and a leukocyte removal ratio (%) is calculated from the two counts of leukocytes.

Shown in Table 1 below are the results of five times of extracorporeal blood circulations, namely, the β-thromboglobulin concentration in the blood, the platelet factor 4 concentration in the blood, the leukocyte removal ratio (an average of five values obtained in the five times of extracorporeal blood circulations), the pressure drop index of the blood treating means, and the degree of the alleviation of clinical symptoms (as evaluated in terms of a decrease in the number of the occurrence of diarrhea per day). As shown in Table 1, in Example 1, in which filter device (α) was used as the blood treating means, the values of the β-thromboglobulin concentration and platelet factor 4 concentration were large, as compared to the corresponding values obtained in Comparative Example 1, in which filter device (β) was used. Further, the degree of the alleviation of clinical symptoms in Example 1 was high, as compared to that in Comparative Example 1. In Table 1, each of the evaluations shown under the item "Degree of alleviation of clinical symptoms" is a comparison between the data obtained before the first time operation of extracorporeal blood circulation and the data obtained after the fifth time operation of extracorporeal blood circulation, and each of the β-thromboglobulin concentration value and the platelet factor 4 concentration value is an average of the five values obtained in the five times of extracorporeal blood circulations.

TABLE 1

|  | Comparative Example 1 | Example 1 |
| --- | --- | --- |
| β-thromboglobulin concentration | 755 ng/ml | 5,790 ng/ml |
| Platelet factor 4 concentration | 433 ng/ml | 1,730 ng/ml |
| Pressure drop index | 10 | 70 |
| Leukocyte removal ratio (%) | 84.0 | 94.8 |
| Degree of alleviation of clinical symptoms (in terms of decrease in the number of the occurrence of diarrhea per day) | Decreased from 10 to 6 | Decreased from 10 to 2 |

EXAMPLE 2 AND COMPARATIVE EXAMPLE 2

In each of Example 2 and Comparative Example 2, for treating a patient suffering from articular rheumatism, an extracorporeal blood circulation system as shown in FIG. 1 was prepared. As blood treating means 4 containing platelet activating means 4A also capable of removing leukocytes, the same filter device as filter device (β) used in Comparative Example 1 was used.

In each of Example 2 and Comparative Example 2, using the above extracorporeal blood circulation system, extracorporeal blood circulation for one hour at a flow rate of 50 ml/minute was performed on an articular rheumatism patient seven times at a frequency of once per week. In Example 2, as the anticoagulant, nafamostat mesilate was continuously added to the collected blood at a rate of 30 mg/hour. In Comparative Example 2, as the anticoagulant, an ACD-A solution was continuously added to the collected blood at a rate of 300 ml/hour.

Shown in Table 2 below are the results of the seven times of extracorporeal blood circulations, namely, the β-thromboglobulin concentration in the blood (an average of the seven values obtained in the seven times of extracorporeal blood circulations), the platelet factor 4 concentration in the blood (an average of seven values obtained in the seven times of extracorporeal blood circulations), the leukocyte removal ratio (an average of the seven values obtained in the seven times of extracorporeal blood circulations), the pressure drop index of the blood treating means, and the degree of the alleviation of clinical symptoms (as evaluated with respect to each of tender joint score, swollen joint score and Ritchie Index, by making a comparison between the data obtained before the first time operation of extracorporeal blood circulation and the data obtained after the seventh time operation of extracorporeal blood circulation). As shown in Table 2, in Example 2, the values of the β-thromboglobulin concentration and platelet factor 4 concentration were large, as compared to the corresponding values obtained in Comparative Example 2. Further, the degree of the alleviation of clinical symptoms in Example 2 was considerably high, as compared to that in Comparative Example 2.

TABLE 2

|  | Comparative Example 2 | Example 2 |
| --- | --- | --- |
| Anticoagulant | ACD-A solution (300 ml/hour) | Nafamostat mesilate (30 mg/hour) |
| β-thromboglobuiin concentration | 847 ng/ml | 4,818 ng/ml |
| Platelet factor 4 concentration | 433 ng/ml | 1,900 ng/ml |
| Pressure drop index | 10 | 60 |

TABLE 2-continued

|  | Comparative Example 2 | Example 2 |
|---|---|---|
| Leukocyte removal ratio (%) | 83.5 | 82.8 |
| Tender joint score | Decreased from 126 to 110 (improved by 13%) | Decreased from 119 to 63 (improved by 47%) |
| Swollen joint score | Decreased from 9 to 6 (improved by 33%) | Decreased from 9 to 3 (improved by 67%) |
| Ritchie Index | Decreased from 17 to 15 (improved by 12%) | Decreased from 14 to 7 (improved by 50%) |

EXAMPLE 3 AND COMPARATIVE EXAMPLE 3

In each of Example 3 and Comparative Example 3, for treating a patient suffering from articular rheumatism, an extracorporeal blood circulation system as shown in FIG. 1 was prepared. As blood treating means 4 containing platelet activating means 4A also capable of removing leukocytes, use was made of filter device (γ) produced by packing 60 g of cellulose acetate beads having a particle diameter of about 2 mm into a cylindrical casing having an inlet and an outlet and having an inner diameter of 2.5 cm and an internal-space length of 23.6 cm.

In each of Example 3 and Comparative Example 3, using the above extracorporeal blood circulation system, extracorporeal blood circulation for one hour at a flow rate of 50 ml/minute was performed on an articular rheumatism patient seven times at a frequency of once per week. In Example 3, as the anticoagulant, heparin was continuously added to the collected blood at a rate of 1,000 units/hour. In Comparative Example 3, as the anticoagulant, nafamostat mesilate was continuously added to the collected blood at a rate of 50 mg/hour.

Shown in Table 3 below are the results of the seven times of extracorporeal blood circulations, namely, the β-thromboglobulin concentration in the blood (an average of the seven values obtained in the seven times of extracorporeal blood circulations), the platelet factor 4 concentration in the blood (an average of the seven values obtained in the seven times of extracorporeal blood circulations), the leukocyte removal ratio (an average of the seven values obtained in the seven times of extracorporeal blood circulations), the pressure drop index of the blood treating means, and the degree of the alleviation of clinical symptoms (as evaluated with respect to each of tender joint score, swollen joint score and Ritchie Index, by making a comparison between the data obtained before the first time operation of extracorporeal blood circulation and the data obtained after the seventh time operation of extracorporeal blood circulation). As shown in Table 3, in Example 3, the values of the β-thromboglobulin concentration and platelet factor 4 concentration were large, as compared to the corresponding values obtained in Comparative Example 3. Further, the degree of the alleviation of clinical symptoms in Example 3 was considerably high, as compared to that in Comparative Example 3.

TABLE 3

|  | Comparative Example 3 | Example 3 |
|---|---|---|
| Anticoagulant | Nafamostat mesilate (50 mg/hour) | Heparin (1,000 units/hour) |
| β-thromboglobulin concentration | 753 ng/ml | 2,032 ng/ml |
| Platelet factor 4 concentration | 338 ng/ml | 901 ng/ml |
| Pressure drop index | 10 | 60 |
| Leukocyte removal ratio (%) | 40.3 | 42.2 |
| Tender joint score | Decreased from 140 to 125 (improved by 11%) | Decreased from 136 to 87 (improved by 36%) |
| Swollen joint score | Decreased from 8 to 6 (improved by 25%) | Decreased from 7 to 4 (improved by 43%) |
| Ritchie Index | Decreased from 22 to 15 (improved by 32%) | Decreased from 19 to 10 (improved by 47%) |

INDUSTRIAL APPLICABILITY

When blood from a patient suffering from an inflammatory disease is treated using the extracorporeal blood circulation system or method of the present invention for treating inflammatory diseases so that the treated blood satisfies the requirement (1) of having a β-thromboglobulin concentration in the range of from 1,000 to 20,000 ng/ml and/or the requirement (2) of having a platelet factor 4 concentration in the range of from 500 to 10,000 ng/ml, a high degree of alleviation of the clinical symptoms of the inflammatory disease can be achieved.

We claim:

1. An extracorporeal blood circulation system for treating inflammatory diseases, comprising:

blood collection means for collecting blood from a patient suffering from an inflammatory disease, anticoagulant mixing means for mixing an anticoagulant into the collected blood, said anticoagulant having the ability to suppress an increase in concentration of at least one platelet factor in the collected blood, said at least one platelet factor being selected from the group consisting of β-thromboglobulin and platelet factor 4, blood transportation means for transporting the anticoagulant-containing blood at a flow rate in the range of from 20 to 200 ml/minute, blood treating means having a blood inlet and a blood outlet and containing platelet activating means having the ability to increase, upon treatment of blood with said blood treating means, the concentration of said at least one platelet factor in the blood, and blood returning means for returning the treated blood to said patient, said blood collection means, said anticoagulant mixing means, said blood transportation means, said blood treating means and said blood returning means being liquid-tightly connected in this order through a tubing, wherein, when extracorporeal blood circulation is conducted using said system with respect to blood from said patient, said system is capable of providing treated blood satisfying at least one requirement selected from the group consisting of the following requirements (1) and (2):

(1) having a β-thromboglobulin concentration in the range of from 1,000 to 20,000 ng/ml, as measured just outside of the blood outlet of said blood treating means; and (2) having a platelet factor 4 concentration in the range of from 500 to 10,000 ng/ml, as measured just outside of the blood outlet of said blood treating means, wherein said blood treating means has a pressure drop index in the range of from 20 to 150, wherein said pressure drop index is defined as a value obtained by a method in which heparin is added to bovine blood having a hematocrit value of about 40% and a total protein of about 6.5 q/dl of plasma so that a final heparin concentration becomes 5 units per ml of said bovine blood; the bovine blood is flowed through said blood treating means at a flow rate of 50 ml/minute, wherein, before the bovine blood enters said blood treating means, the same anticoagulant as used in a treatment of said patient with said extracorporeal blood circulation system is mixed into said bovine blood in the same manner as in said treatment of the patient; a blood pressure difference (mmHg) as between the blood inlet and blood outlet of said blood treating means is measured 20 minutes after the start of the flowing of said bovine blood; and said blood pressure difference is taken as a pressure drop index.

2. The extracorporeal blood circulation system according to claim 1, wherein said blood treating means is a module comprising a casing having a blood inlet and a blood outlet, and said platelet activating means packed therein, said platelet activating means comprising a material comprised mainly of at least one member selected from the group consisting of fibers, a porous material, particles, a film, a planar membrane, a hollow fiber membrane and a tubular material.

3. The extracorporeal blood circulation system according to claim 1, wherein said platelet activating means is capable of removing leukocytes.

4. An extracorporeal blood circulation method for treating inflammatory diseases, comprising:

collecting blood from a patient suffering from an inflammatory disease, mixing an anticoagulant into the collected blood, said anticoagulant having the ability to suppress an increase in concentration of at least one platelet factor in the collected blood, said at least one platelet factor being selected from the group consisting of β-thromboglobulin and platelet factor 4, transporting the blood having said anticoagulant mixed thereinto, at a flow rate in the range of from 20 to 200 ml/minute to blood treating means having a blood inlet and a blood outlet and containing platelet activating means having the ability to increase, upon treatment of blood with said blood treating means, the concentration of said at least one platelet factor in the blood, passing the blood through said blood treating means from said inlet to said outlet to treat the blood, and returning the treated blood to said patient, said treated blood satisfying at least one require ment selected from the group consisting of the following requirements (1) and (2):

(1) having a β-thromboglobulin concentration in the range of from 1,000 to 20,000 ng/ml, as measured just outside of the blood outlet of said blood treating means; and (2) having a platelet factor 4 concentration in the range of from 500 to 10,000 ng/ml, as measured just outside of the blood outlet of said blood treating means, wherein said blood treating means has a pressure drop index in the range of from 20 to 150, wherein said pressure drop index is defined as a value obtained by a method in which heparin is added to bovine blood having a hematocrit value of about 40% and a total protein of about 6.5 q/dl of plasma so that a final heparin concentration becomes 5 units per ml of said bovine blood; the bovine blood is flowed through said blood treating means at a flow rate of 50 ml/minute, wherein, before the bovine blood enters said blood treating means, the same anticoagulant as used in a treatment of said patient with said extracorporeal blood circulation system is mixed into said bovine blood in the same manner as in said treatment of the patient; a blood pressure difference (mmHg) as between the blood inlet and blood outlet of said blood treating means is measured 20 minutes after the start of the flowing of said bovine blood; and said blood pressure difference is taken as a pressure drop index.

5. The extracorporeal blood circulation method according to claim 4, wherein said blood treating means is a module comprising a casing having a blood inlet and a blood outlet, and said platelet activating means packed therein, said platelet activating means comprising a material comprised mainly of at least one member selected from the group consisting of fibers, a porous material, particles, a film, a planar membrane, a hollow fiber membrane and a tubular material.

6. The extracorporeal blood circulation method according to claim 4, wherein said platelet activating means is capable of removing leukocytes.

* * * * *